United States Patent
Song

(10) Patent No.: US 8,784,689 B2
(45) Date of Patent: Jul. 22, 2014

(54) COLOR-CHANGING COMPOSITION

(75) Inventor: Xuedong Song, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 13/178,766

(22) Filed: Jul. 8, 2011

(65) Prior Publication Data

US 2012/0143160 A1  Jun. 7, 2012

Related U.S. Application Data

(60) Provisional application No. 61/419,981, filed on Dec. 6, 2010.

(51) Int. Cl.
 *G01N 31/22* (2006.01)

(52) U.S. Cl.
 USPC ........ 252/408.1; 422/400; 422/420; 436/164; 436/169; 604/358; 604/361

(58) Field of Classification Search
 USPC .......... 422/400, 420; 436/164, 169; 604/358, 604/361; 252/408.1
 See application file for complete search history.

(56) References Cited

U.S. PATENT DOCUMENTS

| | | |
|---|---|---|
| 5,130,290 A | 7/1992 | Tanimoto |
| 5,197,958 A | 3/1993 | Howell |
| 6,793,721 B2 | 9/2004 | Shen et al. |
| 7,105,715 B2 | 9/2006 | Carlucci et al. |
| 2004/0087922 A1 | 5/2004 | Bobadilla |
| 2005/0234415 A1 | 10/2005 | Liu |
| 2006/0114754 A1 | 6/2006 | MacDonald et al. |
| 2006/0287215 A1 | 12/2006 | McDonald et al. |
| 2007/0012218 A1 | 1/2007 | Jang et al. |
| 2007/0252115 A1 | 11/2007 | Arehart et al. |
| 2007/0265591 A1 | 11/2007 | Loritz et al. |
| 2007/0270773 A1 | 11/2007 | Mackey |
| 2008/0021423 A1 | 1/2008 | Klofta et al. |
| 2008/0057532 A1 | 3/2008 | Martin et al. |
| 2008/0145940 A1 | 6/2008 | Menon |
| 2008/0145948 A1* | 6/2008 | Menon .................... 436/164 |
| 2009/0143516 A1 | 6/2009 | MacDonald et al. |
| 2009/0157025 A1 | 6/2009 | Song et al. |
| 2009/0325221 A1 | 12/2009 | Long et al. |
| 2009/0326409 A1 | 12/2009 | Cohen et al. |
| 2010/0012017 A1 | 1/2010 | Miller |
| 2010/0030173 A1 | 2/2010 | Song et al. |
| 2011/0144603 A1 | 6/2011 | Song |

* cited by examiner

*Primary Examiner* — Monique Cole
(74) *Attorney, Agent, or Firm* — Denise L. Stoker

(57) ABSTRACT

The present invention relates to a color-changing composition and a multiple-component material including a substrate and a printed layer on the substrate. The printed layer includes a color-changing composition to indicate a change in condition, such as a change in wetness. The color-changing composition includes a matrix-forming component, a leuco dye, a Lewis Acid, a neutral surfactant and an organic solvent.

19 Claims, No Drawings

COLOR-CHANGING COMPOSITION

This application claims priority to provisional application Ser. No. 61/419,981 entitled "Color-Changing Composition" and filed in the U.S. Patent and Trademark Office on Dec. 10, 2010. The entirety of provisional application Ser. No. 61/419,981 is hereby incorporated by reference.

FIELD OF THE INVENTION

The present invention relates to a homogenous, color-changing composition that includes a matrix-forming component, a leuco dye, a Lewis Acid, a neutral surfactant and an organic solvent. The homogenous, color-changing composition may be printed upon a substrate. The homogenous, color-changing composition can cause the printed substrate to change in appearance of its color when the printed substrate is exposed to a change in physical or chemical environment. For example, the printed substrate may be a nonwoven material that is used as a component of an absorbent article. The homogenous, color-changing composition may become colorless in response to the presence of urine.

BACKGROUND OF THE INVENTION

Many products, including consumer and professional products, are more effectively used by an end user when they include a feature that indicates a particular condition or degree of use. An example of a visual indicator is a color indicator. Color indicators can either indicate a change in condition or a degree of use through a change from "color" to "no color" (or vice versa) or through a change from one color to a different color.

Exemplary conditions that could be monitored using a color indicator include physical conditions such as the presence of moisture and chemical conditions. Exemplary consumer products that could be more effective and deliver more benefits to end users by incorporating a suitable color indicator include absorbent articles, facial tissues, bath tissue, paper towels, household cleaning items and personal cleaning wipes. Exemplary professional products that could be more effective and deliver more benefits to end users by incorporating a suitable color indicator include products for medical use, safety garments, industrial cleaning products and nonwoven materials.

Color indicators are well known and are available in various forms. Desirable performance attributes include durability and good retention (i.e. the color indicator remains where intended and does not leach out into other components of the product within which it is being used). Depending on the product application, it may also be desirable to have the structure in which the color indicator is used be wettable, but water-insoluble. It may also be desirable for the color indicator to have a distinct, or sharp, color change and a rapid response time to aid the user in identifying the physical condition change in the product. For purposes of applying the color indicator to a component of a product, it may also be desirable to have a color indicator that can be applied in liquid form at room temperature (American Society of Heating, Refrigerating and Air-Conditioning Engineers, Inc. (ASHRAE) standard range of 20° C. to 25° C. at 40% to 60% relative humidity). When the color indicator is in a liquid form at room temperature, the color indicator can be easily printed (just like an ink composition) onto the desired component of a product.

Examples of how color indicators are already incorporated into consumer products include diapers that have wetness sensors. Some of the wetness sensors used in diapers lose color to indicate wetness while others develop color in response to wetness (i.e. the color appears when the indicator is dissolved by water). The concept of incorporating a color-changing composition into a wearable article (such as a disposable diaper) is known in the art. For example, U.S. Patent Application Publication No. 2010/0030173 by Song et al. (hereinafter "the '173 publication") is directed to a wetness sensor for an absorbent article. The color-changing composition of the '173 publication includes an electron-donating leuco dye and an electron deficient receptor. The wetness-indicating composition may include surfactants. The surfactants may be non-ionic surfactants, ionic surfactants or a mixture thereof. The wetness-indicating composition of the '173 publication transitions from a color, to a weaker color and perhaps will become colorless in response to water-containing liquids. The wetness-indicating composition of the '173 publication can fade color with prolonged exposure and increased amounts of a water-containing liquid. The strong color of the indicating materials begins to fade in proportion to the amount and contact time with a water-containing liquid (i.e. the composition is able to indicate different degrees or levels of wetness over time). While the wetness-indicating compositions of the '173 publication are capable of becoming colorless, the compositions do not provide rapid and distinct color change after exposure to water-containing liquids. The surfactant of the '173 publication composition is not necessary to invoke the disappearance of color.

Another example of color-changing compositions known in the art is ink used with writing instruments. It is sometimes desirable to remove ink that has been accidentally written on paper, walls or furniture. For example, U.S. Pat. No. 5,417,748 by Kawashima (hereinafter "the '478 patent") is directed to a writing instrument that contains a color ink agent. The color ink agent of the '478 patent consists of certain electron donative coloring compounds and certain electron acceptive developing compounds. The color ink agent of the '478 patent changes from a state of color to a state of becoming colorless in response to water-containing liquids. The color ink agent of the '478 patent is intended for convenient and clean erasure of the ink from a surface. The color ink agent of the '478 patent doesn't require the need to maintain the ink on a preprinted surface until it is desired for the composition to change color. The color ink agent of the '478 patent also does not require the need for rapid and distinct color change. As a result, the '478 patent does not address the need for additional components in the color ink agent beyond electron donative coloring compounds and electron acceptive developing compounds.

While the color-changing compositions known in the art provide certain benefits, there remains a need for a composition that shows rapid and distinct, or acute, color change for ease of reading when the composition is used in a product. There also remains a need for the composition to be durable and remain where intended in the product. When the purpose of the composition is to detect the presence of wetness, there remains a need for a composition that is water-resistant and water-insoluble. There remains a need for a composition that can be printed on a substrate. Further, there remains a need for a composition that can be applied, such as by printing, at room temperature so that the composition can be applied to a substrate without heating. In addition to the needs identified above, there are unmet needs associated with using multi-component materials as components of personal care absorbent articles, such as disposable diapers. In particular, there is a need for a color-changing composition that maintains its efficacy when used in conjunction with outer cover material.

SUMMARY OF THE INVENTION

The present invention is directed to a homogenous, color-changing composition that includes a matrix-forming component, a leuco dye, a Lewis Acid, a neutral surfactant and an organic solvent. The leuco dye and the Lewis Acid form colored complexes when the color-changing composition is in a dry state. The mechanism for the color to disappear from the composition includes the introduction of an aqueous based liquid (e.g. water or urine) to the color-changing composition.

In another aspect, the present invention is directed to a multiple-component material that includes a printed layer formed on a substrate. The printed layer includes a homogeneous color-changing composition. The homogeneous color-changing composition includes a matrix-forming component, a leuco dye, a Lewis Acid and a neutral surfactant.

In yet another aspect, the present invention is directed to a disposable absorbent article including a multiple-component material that includes a substrate and a film layer on the substrate. The film layer includes a color-changing composition that includes 20% to 95% of a matrix-forming component; 0.1% to 10% of a leuco dye; 1% to 20% of a Lewis Acid; and 2% to 50% of a neutral surfactant.

These aspects and additional aspects of the invention will be described in greater detail herein. Further, it is to be understood that both the foregoing general description and the following detailed description are exemplary and are intended to provide further explanation of the invention claimed.

DETAILED DESCRIPTION OF THE INVENTION

The present disclosure of the invention will be expressed in terms of its various components, elements, constructions, configurations, arrangements and other features that may also be individually or collectively be referenced by the term, "embodiment(s)" of the invention, or other similar terms. It is contemplated that the various forms of the disclosed invention may incorporate one or more of its various features and embodiments, and that such features and embodiments may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The present invention is directed to a homogenous, color-changing composition that includes a matrix-forming component, a leuco dye, a Lewis Acid, a neutral surfactant and an organic solvent. The matrix-forming component can be a water-insoluble, film-forming polymer or an ink base, such as a varnish having an organic solvent base. The leuco dye may be selected from phthalide type or fluoran type dyes. The Lewis Acid may be a metal salt-based Lewis Acid. The neutral surfactant may be a neutral block copolymer surfactant. The color-changing composition may be dissolved in an organic solvent.

In particular, the invention relates to a color-changing composition that contains at least one leuco dye and at least one Lewis Acid. The leuco dye is an electron-donating component and the Lewis Acid is an electron-accepting component. The leuco dye and the Lewis Acid form colored complexes when the color-changing composition is in a dry state. The mechanism for the color to disappear from the composition includes the introduction of an aqueous based liquid (e.g. water or urine) to the color-changing composition. The Lewis Acid is more attracted to the water than the leuco dye and the color disappears from the composition. The composition may serve as a wetness indicator by rapidly and distinctly becoming colorless in the presence of water as the Lewis Acid becomes more attracted to the water and disassociates from the leuco dye.

The matrix-forming component of the color-changing composition can include one or more water-insoluble, film-forming polymers and/or one or more ink bases, such as a varnish having an organic solvent base. In part, the functions of the matrix-forming component are to provide a binding matrix to keep other components of the color-changing composition, such as the surfactant, leuco dye and Lewis Acid, from significant leaching when wetted and to provide a suitable viscosity required for printing. Benefits of the color-changing composition including a film-forming polymer include that the composition adheres effectively to the substrate which prevents the composition from cracking off of the substrate when the composition is dry. The colored complex is less likely to leach away from or out of the color-changing composition in the presence of water or urine when the water-insoluble polymers and/or varnishes are included in the color-changing composition.

The matrix-forming component may also or alternatively include an ink base material. The ink base material may include a small molecule, a polymeric material or a mixture of small molecules and polymers. Another suitable ink base material for the color-changing compositions of the invention is a varnish base such as a nitrocellulose compound-based varnish, ethyl cellulose-based varnish, polyurethane-based binding systems or a phenolic-modified co-solvent-type polyamide resin-based varnish. It is believed that the ink base material may help the stability of the color-changing composition. It is also believed that the ink base material may improve the adhesion of the color-changing composition to the substrate. The ink base material may be water-insoluble.

The neutral surfactant in the color-changing composition can be a neutral block copolymer surfactant comprising blocks of two different poly(alkylene oxides). These neutral block copolymer surfactants can be selected from polyoxypropylene-polyoxyethylene block copolymer, poly[poly(ethylene oxide)-block-poly(propylene oxide)]copolymer or propylene glycol-ethylene glycol block copolymer. The neutral block copolymer acts as a wettability agent and provides good solubility in both alcohol-based solvents and water. The leuco dye may be selected so that it responds by changing color to a particular physical or chemical condition. The charged leuco dye forms a colored complex with the oppositely charged Lewis Acid. The colored complex of leuco dye and Lewis Acid is not significantly affected by the neutral surfactant as opposed to if a charged surfactant were used in the color-changing composition. The neutral surfactant preserves the leuco dye/Lewis Acid colored complex—and provides good wettability without a significant reduction in color intensity. A charged surfactant significantly reduces the color intensity by negatively impacting the formation of the complex of leuco dye and the Lewis Acid in the color-changing composition.

The color-changing composition is liquid at room temperature and may be applied as an ink to the substrate, such as by printing, spraying or stamping. The color-changing composition may be dissolved in an organic solvent that acts as a carrier and later evaporates after the color-changing composition is applied to the printed layer or forms the printed layer itself. The organic solvent in the color-changing composition can be a low molecular weight alcohol selected from ethanol, propanol and butanol. The organic solvent may also be selected from acetone, tetrahydrofuran, benzene, toluene and acetonitrile.

The color-changing composition is a homogenous mixture. The composition remains visually clear, shows no precipitation when the composition is centrifuged at a rate of up to 14,000 revolutions per minute and no precipitation of the composition was observed after a two year period without any external agitation force. Many types of ink compositions are not homogeneous. For example, some ink compositions suspend pigment particles that are in an ink matrix. Some ink compositions use particles that are encapsulated with dyes which are also suspended in an ink matrix. Other ink compositions are emulsion-based that include more than one phase. Heterogeneous ink compositions which have multiple phases are intrinsically not the most stable ink compositions. Therefore, heterogeneous ink compositions have limited lifetime due to their inherent instability. The homogeneous ink compositions of the present invention have only one phase and are more stable than heterogeneous inks.

Unlike prior color-changing compositions, the color-changing compositions of the present invention are liquid at room temperature and can be applied to a substrate without heating. For example, the color-changing composition may be printed like an ink onto a substrate at room temperature. This feature of the color-changing compositions makes them easier to handle during the manufacture of the absorbent articles to which they are applied. Further, the color-changing compositions of the present invention form a film-like layer when they are applied, such as by printing, to a substrate and dried. A benefit of the color-changing composition forming a film on the substrate is to afford good adherence to the substrate and to prevent cracking of the composition.

When in the form of a film layer on a substrate, the color-changing compositions of the invention are wettable but insoluble in water. This feature makes the color-changing compositions desirable for use in articles where the compositions will be exposed to wetness. The feature also results in color-changing compositions that are durable and that are resistant to leaching out of the film-like printed layer. The printed layer may be formed on the substrate in a desired pattern including stripes, dots, geometric shapes and irregular shapes and combinations of such pattern elements. The printed layer may also be formed on the substrate as an alpha-numeric character, an anthropomorphic image, a pictorial representation of an animal, a pictorial representation of an inanimate object, a cartoon character, a product or company logo and a trademark or brand or combinations of such pictorial elements.

In one aspect, the present invention is directed to a multiple-component material that includes a substrate and a printed layer. The substrate may be in the form of a porous foam, a reticulated foam, cellulose tissues, a plastic film, a woven material or a nonwoven material. Suitable plastic films that may be used to form the substrate include polyethylene films and polypropylene films. Suitable woven materials include woven materials made from natural fibers, synthetic fibers or combinations of natural and synthetic fibers. Natural fibers include cotton, silk and wool fibers and synthetic fibers include polyester, polyethylene and polypropylene fibers. Suitable nonwoven materials include nonwoven materials made through traditional techniques such as spunbond, melt-blown and bonded carded web materials. The spunbond, meltblown and bonded carded web materials may be made from suitable synthetic fibers such as polyester, polyethylene and polypropylene fibers. The substrate may include combinations of the materials identified above such as a substrate that includes both a porous foam and a nonwoven material or a substrate that includes both a plastic film and a nonwoven material.

The multiple-component materials of the invention also include a printed layer that is adhered to the substrate. The printed layer includes a color-changing composition. The printed layer may be formed by the color-changing composition itself or the color-changing composition may be applied to or incorporated into the printed layer. Because the color-changing compositions of the invention are liquid at room temperature, they can be applied through printing or stamping either directly onto the substrate (thereby self-forming the printed layer) or onto a pre-existing layer having a film-like structure and associated with the substrate.

The color-changing composition includes a matrix-forming component. The matrix-forming component may include one or more water-insoluble, film-forming polymers and/or one or more ink base materials. The matrix-forming component of the color-changing composition forms the medium to keep the leuco dye, the Lewis Acid and surfactant in proximity to each other. By forming the medium, the matrix-forming component enables the performance of the color-changing composition to be wettable, but water-insoluble; and to remain as a film layer on the substrate as opposed to migrating/leaching away from the substrate.

The water-insoluble, film-forming polymers are solid at room temperature, but soluble in an organic solvent or an organic mixing solvent so that when used, the color-changing composition is liquid at room temperature. The ink base materials are dissolved in a liquid solution at room temperature. When an ink based material is included in the matrix-forming component, an organic solvent may or may not be used. Desirably, the water-insoluble, film-forming polymers/copolymers have a substantial amount, greater than about 0.5% by weight, of polar atoms such as oxygen and nitrogen. The polar atoms may be present in polar functional groups such as amides, carboxylic acids and esters. Preferably, the water-insoluble polymers/copolymers are soluble in an organic solvent such as ethanol, acetone, methanol, acetonitrile, tetrahydrofuran, benzene, toluene and mixtures of such solvents.

The water-insoluble, film-forming polymer and the other components of the color-changing composition can be dissolved in the organic solvent prior to application onto the substrate. The organic solvent is a vehicle for the composition to be applied to a substrate. When the mixture of the color-changing composition and the organic solvent is formed, the mixture is a homogeneous, liquid solution at room temperature. The organic solvent evaporates when the color-changing composition is either applied to the printed layer or forms the printed layer. The organic solvent may be a single solvent or a mixture of solvents. Suitable solvents to carry the color-changing composition include ethanol, isopropanol, acetone, methanol, acetonitrile, tetrahydrofuran, benzene and toluene. More than one organic solvent may be used.

The color-changing compositions of the invention include a matrix-forming component in an amount of from 20% to 95% of the total weight of the color-changing composition. Desirably, the color-changing compositions of the invention include a matrix-forming component in an amount of from 20% to 90% of the total weight of the color-changing composition.

Suitable water-insoluble, film-forming polymers include acrylate/acrylamide copolymers, polyurethane adhesives, copolymers of vinylpyrrolidone and copolymers of dimethyl aminopropyl methacrylamide. Commercially-available suitable polymers include DERMACRYL 79 polymer and AMPHOMER HC polymer, both of which are acrylate/octylacrylamide copolymers available from Akzo Nobel. Another example of a commercially-available suitable polymer is GANTREZ SP polymer, which is a monoalkyl ester of poly (methyl vinyl ether/maleic acid) copolymer available from International Specialty Products Inc.

Suitable ink base materials may be small molecules, polymeric materials or a mixture of small molecules and polymers. Examples of suitable small molecule base materials include glycols, including triglycerols and their derivatives. Examples of suitable polymeric materials that may be used as ink base materials include polyvinyl alcohol, polyvinyl pyrrolidone, polyethylene glycol, water-soluble derivatives of polyacrylates and polyacrylamides, poly(hydroxyethyl methacrylates), poly(hydroxylethyl acrylates), carboxymethyl cellulose, methyl cellulose, ethyl cellulose, gelatin and gum Arabic. Another suitable ink base material for the color-changing compositions of the invention is a varnish base such as a nitrocellulose compound based varnish or a phenolic-modified co-solvent-type polyamide resin-based varnish. Further, the ink base material can be a varnish having an organic solvent base. It is believed that the ink base material may help the stability of the color-changing composition. It is also believed that the ink base material may improve the adhesion of the color-changing composition to the substrate of the multiple-component material. The ink base material may be water-soluble or water-insoluble.

The color-changing composition of the invention also includes at least one leuco dye colorant. The leuco dye is an electron-donating dye selected from phthalide or fluoran type dyes. Phthalide type leuco dyes include arylmethane phthalides, such as triarylmethane phthalides and diarylmethane phthalides, monoheterocyclic substituted phthalides such as, heterocyclic substituted phthalides, diarylmethylazaphthalides, bisheterocyclic substituted phthalides, 3-heterocyclic substituted azaphthalides, 3,3-bisheterocyclic substituted azaphthalides, alkenyl substituted phthalides, bridged phthalides and bisphthalides. Specific examples of phthalide type leuco dyes include: 3,3-bis(p-dimethylaminophenyl)-6-dimethylaminophthalide; 3,3-bis(p-dimethylaminophenyl)phthalide; 3-(p-dimethylaminophenyl)-3-(1,2-dimethylindol-3-yl)phthalide; 3-(p-dimethylaminophenyl)-3-(2-methylindol-3-yl)phthalide; 3,3-bis(1,2-dimethylindol-3-yl)-5-dimethylaminophthalide; 3,3-bis(1,2-dimethylindol-3-yl)-6-dimethylaminophthalide; 3,3-bis(9-ethylcarbazol-3-yl)-6-dimethylaminophthalide; 3,3-bis(2-phenylindol-3-yl)-6-dimethylaminophthalide; 3-p-dimethylaminophenyl-3-(1-methylpyrrol-3-yl)-6-dimethylaminophthalide; 3,3-bis(1-n-butyl-2-methyl-3-indolyl)phthalide; 3,3-bis(4-diethylamino-2-ethoxyphenyl)-4-azaphthalide and 3-(4-diethylamino-2-ethoxyphenyl)-3-(1-ethyl-2-methyl-3-indolyl)-4-azaphthalide.

Fluoran leuco dyes include 3',6'-dimethoxyfluoran; N-acetylauramine; N-phenylauramine; 3,6-dihexyloxyfluoran; 2'-chloro-6'-aminofluoran; 3,6-bis (diethylamino) fluoran-γ-(4'-nitro)-anilinolactam; 2'-chloro-6'-diethylaminofluoran; rhodamine B lactam; 6-diethylamino-benzo[a]fluoran; 2-(phenylimino ethanedilidene)-3,3-trimethyl-indoline; 3',6'-bis-(diphenylamino)fluoran; crystal violet lactone; benzoyl leucomethylene blue; ethyl leucomethylene blue; methoxybenzoyl leucomethylene blue; 2',6'-bis(diethyl-amino)fluoran; malachite green lactone; 2'-anilino-3'methyl-6'-(N-methyl-N-n-propylamino)fluoran; 3-cyclohexyl methylamino-6-methyl-7-anilinofluoran; 1,3,3-trimethyl-indolino-7'-chloro-β-naphthospiropyran and di-β-naphthospiropyran. The color-changing compositions of the invention include a leuco dye in an amount of from 0.1% to 10% of the total weight of the color-changing composition. Desirably, the color-changing compositions of the invention include a leuco dye in an amount of from 0.5% to 5% of the total weight of the color-changing composition. The color-changing compositions of the invention may include more than one leuco dye. One or more leuco dyes that have visually different colors may be combined or leuco dyes having the same visual color may be combined.

The color-changing composition of the invention includes at least one Lewis Acid. The color-changing compositions of the invention may include a mixture of more than one Lewis Acid. The Lewis Acid is an electron-accepting component. Desirably, Lewis Acid is a metal salt-based Lewis Acid. The salt of an aromatic carboxylic acid with polyvalent metals such as zinc, magnesium, aluminum, calcium, titanium, manganese, tin or nickel may also be used as the metal salt-based Lewis Acid. The metal salt based-Lewis Acid may be selected from zinc chloride, zinc salicylate, zinc nitrate, aluminum chloride, aluminum nitrate, aluminum sulfate, magnesium chloride and stannic chloride. Desirably, the color-changing compositions of the invention include a metal salt-based Lewis Acid in an amount of from 1% to 20% of the total weight of the color-changing composition. The charged leuco dye forms a colored complex with the oppositely charged Lewis Acid.

The color-changing composition of the invention may also include a neutral surfactant. The neutral surfactant adjusts the wettability of the composition so that liquids, like urine, can penetrate the composition to break up the colored complex formed between the leuco dye and the Lewis Acid, resulting in a change of the composition to become colorless. The neutral surfactant does not significantly impact the formation of leuco dye and Lewis Acid colored complexes when present in a moderate amount, for example, 1 to 20% of the total weight of the color-changing composition. The neutral surfactant, when present in the color-changing composition in a moderate amount, makes the composition wettable without significant, negative affects to the color intensity of the color-changing composition. Charged surfactants can desensitize the complex formation and significantly diminish the color intensity of the color-changing composition when present in a moderate amount. One dimension of the performance of the color-changing compositions of the invention is their response time. Response time can be improved by increasing the wettability of the color-changing composition (by increasing the amount of surfactant) so that liquids can penetrate more rapidly. Including a neutral surfactant can increase wettability without significantly affecting the initial color intensity of the color-changing composition. For example, the use of charged surfactants, while providing wettability, will significantly inhibit the formation of the leuco dye and Lewis Acid complex with the additional charge interference provided by the charged surfactant. Charged surfactants will cause the color intensity of the composition to be very weak or to have no color at all. Therefore, use of neutral surfactants in the color-changing composition results in compositions with improved wettability, good stability and intense color prior to exposure with a water-containing liquid.

The neutral surfactant may be a small molecule or a polymer. It is believed that the addition of a neutral surfactant to the color-changing composition will improve response speed by increasing the wettability of the color-changing composition. Suitable neutral polymeric surfactants include TWEEN surfactants, such as TWEEN 20 surfactant, TWEEN 40 surfactant and TWEEN 80 surfactant, and TRITON X-100 surfactant, which are available from Sigma-Aldrich, Incorporated. Other suitable neutral surfactants include polyethylene lauryl ether, polyoxyethylene nonyl phenyl ether, polyoxyethylene oleyl phenyl ether, polyoxyethylene sorbitan monolaurate, polyethylene glycol monostearate, polyethylene glycol sorbitan monolaurate, polyoxyethylenesorbitan monopalmitate, polyoxyethylenesorbitan monostearate, polyoxyethylenesorbitan monooleate, polyoxyethylenesorbitan trioleate, polypropylene glycol sorbitan monolaurate, polyoxypropylenesorbitan monopalmitate, polyoxypropylenesorbitan monostearate, polyoxypropylenesorbitan monooleate, polyoxypropylenesorbitan trioleate, polyalkyne glycol sorbitan monolaurate, polyalkyne glycol sorbitan monopalmitate, polyalkyne glycol sorbitan monostearate, polyalkyne glycol sorbitan monooleate, polyalkyne glycol sorbitan trioleate and mixtures of such neutral surfactants.

Additional suitable neutral surfactants include neutral block copolymer based surfactants. The neutral block copolymer based surfactants include FLU RON IC series block copolymers, such as PLURONIC P84 or FLU RON IC P85 surfactants, which are available from BASF Corporation. Other suitable neutral block copolymer based surfactants include nonylphenol ethoxylates, linear alkyl alcohol ethoxylate, ethylene oxide-propylene oxide block copolymer, polyoxypropylene-polyoxyethylene block copolymer, polyalkylene oxide block copolymer, polyalkylene oxide block copolymer and propylene glycol-ethylene glycol block copolymer.

The color-changing compositions of the invention include neutral surfactants in an amount of from 2% to 50% of the total weight of the color-changing composition. The color-changing compositions of the invention may include more than one neutral surfactant. The color-changing compositions of the invention do not include any charged surfactants and are therefore free of cationic and anionic surfactants. The color-changing compositions of the invention do not include charged surfactants because it is believed the charged surfactants would interfere with the complex between the leuco dye and the Lewis Acid.

The relative amounts of the components of the color-changing composition may be selected to be present in optimal ratios. For example, it is desirable for the weight ratio of the Lewis Acid to leuco dye be greater than 3. Considering the relative amounts in terms of molar quantities, it is desirable that the molar ratio of the Lewis Acid to leuco dye should range from 2 to 50. Additionally, it is desirable for the weight ratio of the neutral surfactant to leuco dye to be less than 10.

The combination of these components results in the color-changing composition of the invention. The result of the color-changing composition forming a printed layer on the substrate is the multiple-component material of the invention. The printed layer of the present invention may be formed on a nonwoven substrate or on a film. In one aspect, the color-changing composition is applied to a nonwoven substrate that is used as a component of a disposable absorbent article. More specifically, the nonwoven substrate may be a spunbond or other nonwoven material that is used to form the outer cover of a disposable diaper. The substrate may also be a polyethylene film that is adhered to a nonwoven material to form the outer cover of a disposable diaper. The substrate may also be a breathable outer cover that allows permeation of oxygen, but not of water or urine. The water-impermeable, film portion of the outer cover can be made "breathable" through incorporation of particles of calcium carbonate.

Because the color-changing compositions of the present invention are liquid at room temperature, they can be easily applied through printing to a substrate, using such printing methods as flexographic printing, gravure printing or any suitable printing method for the given substrate. Because the outer cover of an absorbent article, such as a disposable diaper, is typically adjacent to the absorbent structure of the article, the color-changing composition is applied to a component that is in proximity to the absorbent structure when the finished product is in use. Therefore, the color-changing composition can be used to indicate a change in condition of the absorbent structure, such as wetness.

In another aspect, the present invention is directed to a multiple-component material that includes a printed layer formed on a substrate. The printed layer includes a color-changing composition that becomes colorless when a change in physical or chemical condition is detected. The multiple-component materials of the invention may be used in personal care articles, such as the outer cover component of a disposable diaper or a training pant. The multiple-component materials of the invention may also be used in the construction of feminine care articles. The color-changing composition includes a matrix-forming component, a leuco dye, a Lewis Acid and a neutral surfactant. When the multiple-component material is used as part of the outer cover component of a disposable diaper, the color-changing composition is in contact with the absorbent core of the diaper where liquid is stored during use.

The leuco dye may be selected so that it responds by changing color to a particular physical or chemical condition. The color-changing composition may include one or more leuco dyes. When more than one leuco dye is used, the leuco dyes may be selected based on the desired effect (e.g. different color, better visibility, etc.).

In another aspect, the present invention is directed to a multiple-component material that includes a substrate and a printed layer on the substrate. The printed layer includes a color-changing composition that includes 20% to 95% of a matrix-forming component; 0.1% to 10% of a leuco dye; 1% to 20% of a Lewis Acid; and 2% to 50% of a neutral surfactant. Similarly, in another aspect, the present invention is directed to a disposable absorbent article including a multiple-component material. The multiple-component material includes a substrate and a printed layer on the substrate. The printed layer includes a color-changing composition that includes 20% to 95% of a matrix-forming component; 0.1% to 10% of a leuco dye; 1% to 20% of a Lewis Acid; and 2% to 50% of a neutral surfactant.

In a different aspect, the present invention is directed to a method of forming a multiple-component material. The method includes a step of mixing the components of a color-changing composition with an organic solvent to form a mixture. The color-changing composition includes a matrix-forming component; a leuco dye; a Lewis Acid and a neutral surfactant. The method also includes a step of applying the mixture to a substrate. After the applying step, the method includes a step of allowing the mixture to dry; during this step of allowing the mixture to dry, the organic solvent evaporates and the color-changing composition of the mixture forms a film on the substrate. Therefore, the presence of the organic solvent is to facilitate the step of applying the mixture to a substrate. The organic solvent does not remain with the color-changing composition after the mixture dries as a film on the substrate. The method of the invention is more efficient and lower cost than known methods because the mixture can be applied to the substrate at room temperature and without heating because the mixture is liquid at room temperature.

An example of a color-changing composition of the invention is a composition that includes an acrylate and octylacrylamide copolymer system as the water-insoluble, film-forming polymer; this polymer can assist adhesion of the leuco dye/Lewis acid complex to the substrate and provide wettability with water resistance. Another example of the color-changing composition of the invention is a composition that includes a polyurethane adhesive with amide functionality as the water-insoluble, film-forming polymer. This water-insoluble, film-forming polymer can be dissolved in an alcohol for application to the substrate (with the alcohol subsequently evaporating). The color-changing compositions of the invention are water-wettable to allow rapid color change of the leuco dye/Lewis acid complex, but are water-insoluble to prevent leaching of the complex. These are desirable performance attributes.

The following are various examples that illustrate aspects of the present invention:

Preparation of Exemplary Color-Changing Composition and Multiple-Component Material #1:

Four samples of color-changing compositions that are examples of the present invention were prepared. Each sample includes a matrix-forming component of a varnish having an organic solvent base (obtained from Sun Chemical Corporation) in an amount of 300 µl. Each sample also includes a leuco dye colorant of crystal violet lactone in an amount of 10 mg, a metal salt-based Lewis Acid of zinc salicylate in an amount of 50 mg/ml and an organic solvent of ethanol in the amount of 750 µl. A different amount of a neutral surfactant, PLURONIC P85 surfactant was then added to each of the 4 samples (200 mg/ml in ethanol); 100 µl (to form "sample 1"), 200 µl (to form "sample 2"), 300 µl (to form "sample 3") and 400 µl (to form "sample 4"), respectively. Each sample of matrix-forming component, leuco dye, metal salt-based Lewis Acid, organic solvent and neutral surfactant was then mixed by vortex for 5 minutes until a homogenous solution was formed.

The multiple-component material was prepared by brushing an amount of each sample of the color-changing composition on a low breathable film material (such as would be used to form the outer cover of a disposable absorbent article) using a disposable foam brush to form a thin film of the composition. The film was allowed to dry under ambient conditions for 2 hours to form a blue color. The color of sample 1 was strong blue, the color of sample 2 was strong blue, the color of sample 3 was weak blue and the color of sample 4 was weak blue. To ensure that the color-changing composition was functioning as expected, a drop of water, synthetic urine or real urine caused the blue color to rapidly disappear.

Preparation of Exemplary Color-Changing Composition and Multiple-Component Material #2:

Four samples of color-changing compositions that are examples of the present invention were prepared. Each sample includes a metal salt-based Lewis Acid of zinc salicylate in an amount of 100 mg/ml, a matrix-forming component of varnish (obtained from Sun Chemical Corporation) in an amount of 400 µl, a combination of neutral surfactants including 36 mg of PLURONIC P85 surfactant and 36 mg of TWEEN 40 surfactant, and an organic solvent of ethanol in the amount of 900 µl. A different leuco dye colorant was then added to each of these 4 samples in the amount of 4 mg, respectively: 3,6-dihexyloxyfluoran; 3,3-bis(4-diethylamino-2-ethoxyphenyl)-4-azaphthalide; 3,6-bis(diethylamino)fluoran-γ-(4'-nitro)-anilinolactam and 3-(4-diethylamino-2-ethoxyphenyl)-3-(1-ethyl-2-methyl-3-indolyl)-4-azaphthalide. Each sample of matrix-forming component, leuco dye, metal salt-based Lewis Acid, organic solvent and neutral surfactant was then mixed by vortex for 5 minutes until a homogenous solution was formed.

The multiple-component material was prepared by brushing an amount of each sample of the color-changing composition on a low breathable film material (such as would be used to form the outer cover of a disposable absorbent article) using a disposable foam brush to form a thin film of the composition. The film was allowed to dry under ambient conditions for 2 hours. The color of sample 1 was yellow, the color of sample 2 was green, the color of sample 3 was pink and the color of sample 4 was blue, respectively. To ensure that the color-changing composition was functioning as expected, a drop of water, synthetic urine or real urine caused each of the 4 colors to rapidly disappear.

Preparation of Exemplary Color-Changing Composition and Multiple-Component Material #3:

Two stock solutions of color-changing compositions were prepared. Color-changing composition 1 contained a leuco dye, 3,3-Bis(1-n-butyl-2-methyl-3-indolyl)phthalide (20 mg/ml), in the amount of 900 µl, a metal salt-based Lewis acid, zinc salicylate (saturated in ethanol) in the amount of 3 ml, neutral surfactant mixture of PLURONIC P85 surfactant (200 mg/ml) and TWEEN 40 surfactant (400 mg/ml) in the amount of 900 µl, and a matrix-forming component of an organic-solvent based varnish (obtained from Sun Chemical Corporation) in the amount of 2 ml. Color-changing composition 2 contained 900 ul of violet 1 (3-(4-Diethylamino-2-ethoxyphenyl)-3-(1-ethyl-2-methyl-3-indolyl)-4-azaphthalide, 20 mg/ml), 3 ml zinc salicylate (saturated in ethanol, 900 ul of a mixture of PLURONIC P85 surfactant (200 mg/ml) and TWEEN 40 surfactant (400 mg/ml), and 2 ml of an organic-solvent based varnish. Each color-changing composition was mixed by vortex for 5 minutes until a homogenous solution was formed. Two samples were then prepared to contain different ratios of color-changing compositions 1 and 2. Sample 1 had 1 ml of color-changing composition 1 and 0.5 ml of color-changing composition 2. Sample 2 had 0.5 ml of color-changing composition 1 and 1 ml of color-changing composition 2.

Two multiple-component materials were prepared by brushing an amount of each of sample 1 and sample 2 of the color-changing compositions on a low breathable film material (such as would be used to form the outer cover of a disposable absorbent article) using a disposable foam brush to form a thin film of the composition. The film was allowed to dry under ambient conditions for 2 hours. The color of sample 1 was reddish purple and the color of sample 2 was bluish purple. To ensure that the color-changing compositions were functioning as expected, a drop of water, synthetic urine or real urine caused each of the 2 colors to rapidly disappear.

Stability Testing of Multiple-Component Materials and Color-Changing Compositions of the Invention:

In order to evaluate stability, the exemplary color-changing compositions and multiple-component materials of example #2 were evaluated. The film materials with the 4 color-changing compositions were incubated in an oven at 40° C. and 75% humidity over a period of 4 days. The film materials were then taken out once a day to visually compare the resulting color with the original color; daily inspection showed little change in color from the original color. The response speed and color change upon contact with synthetic urine or water or real urine samples were also visually examined and compared qualitatively; the colors disappeared rapidly.

Comparative Example of the Color-Changing Compositions of the Invention with a Commercial Ink Color-Changing Composition:

In order to evaluate dye leaching, the color-changing composition of the present invention was compared to a commercially-available, color-changing ink composition. The commercially-available, color-changing ink composition was obtained from a PAPY ECO "Water Clear Pen" which contained blue ink. The PAPY ECO "Water Clear Pen" containing blue ink is intended for use as a whiteboard marker. Anything that is written on a whiteboard with the PAPY ECO "Water Clear Pen" will disappear from the board when the ink comes in contact with moisture. The PAPY ECO "Water Clear Pen" was marked with patent number, JP 3329505 B2, which is the Japanese equivalent to the '478 patent.

A total of 10 samples were prepared. Five of the samples include a matrix-forming component of a varnish (obtained from Sun Chemical Corporation) having an organic solvent base in an amount of 300 µl. Each of these 5 samples also includes a leuco dye of crystal violet lactone in an amount of 10 mg, a metal salt-based Lewis Acid of zinc salicylate in an amount of 50 mg/ml and an organic solvent of ethanol in the amount of 750 µl. An amount of 200 µl of a neutral surfactant, PLURONIC P85, was then added to each of the 5 samples (200 mg/ml in ethanol). Each sample of matrix-forming component, colorant, metal salt-based Lewis Acid, organic solvent and neutral surfactant was then mixed by vortex for 5 minutes until a homogenous solution is formed.

The additional 5 samples were prepared using the blue, commercially-available, color-changing ink composition from one or more PAPY ECO "Water Clear Pens".

The multiple-component material was prepared by brushing an amount of each of the 10 samples of the color-changing composition onto a size 5 cm×5 cm piece of low breathable film material (such as would be used to form the outer cover of a disposable absorbent article) using a disposable foam brush to form a thin film of the composition. The film was allowed to dry under ambient conditions for 2 hours.

Each of the 10 samples was incubated for 12 hours at 37° C. An amount of synthetic urine was applied to each of the 10 samples. The synthetic urine that ran off of each sample was analyzed to determine the amount of leuco dye, crystal violet lactone, which leached out of the color-changing compositions by the synthetic urine. The concentration of crystal violet lactone in the runoff synthetic urine for the first 5 samples (the composition of the present invention) averaged 39.3 mg/sample. This concentration is, at a minimum, four times less than the amount that was found in the synthetic urine runoff of the samples from the PAPY ECO "Water Clear Pens". This experiment demonstrates that the ink composition of the present invention leached or lost much less leuco dye into the synthetic urine than the amount of the leuco dye that leached into the synthetic urine when the commercially-available ink composition was used.

While the color-changing compositions and multiple-component materials of the invention have been described in detail with respect to specific aspects thereof, it will be appreciated that those skilled in the art, upon attaining an understanding of the foregoing, may readily conceive of alterations to, variations of and equivalents to these materials. Accordingly, the scope of the present invention should be assessed as that of the claims and any equivalents thereto.

I claim:

1. A homogenous, color-changing liquid composition comprising:
    a matrix-forming component;
    a leuco dye;
    a Lewis Acid;
    a neutral surfactant; and
    an organic solvent; wherein the color-changing composition is capable of changing color when contacted by an aqueous-based liquid, causing the Lewis Acid to dissociate from the leuco dye.

2. The homogenous color-changing composition of claim 1, wherein a molar ratio of the Lewis Acid to leuco dye ranges from 2 to 50.

3. The homogenous color-changing composition of claim 1, wherein a weight ratio of the neutral surfactant to leuco dye is less than 10.

4. The homogenous color-changing composition of claim 1, wherein the matrix-forming component is selected from one or more water-insoluble, film-forming polymers and copolymers.

5. The homogenous color-changing composition of claim 4, wherein the water-insoluble, film-forming polymers and copolymers are selected from acrylate/acrylamide copolymers, polyurethane adhesives, methyl cellulose and copolymers of vinylpyrrolidone and dimethylaminopropyl methacrylamide.

6. The homogenous color-changing composition of claim 1, wherein the matrix-forming component is selected from a varnish and a small molecule and/or polymeric material.

7. The homogenous color-changing composition of claim 1, wherein the color-changing composition includes more than one leuco dye.

8. The homogenous color-changing composition of claim 1, wherein the leuco dye is selected from fluoran leuco dyes, phthalide-type leuco dyes and mixtures thereof.

9. The homogenous color-changing composition of claim 1, wherein the color-changing composition includes more than one Lewis Acid.

10. The homogenous color-changing composition of claim 1, wherein the Lewis acid is selected from zinc salts, iron salts of chloride and salicylate and mixtures thereof.

11. The homogenous color-changing composition of claim 1, wherein the color-changing composition includes more than one neutral surfactant.

12. The homogenous color-changing composition of claim 1 wherein the neutral surfactant is selected from polyethylene glycol-based surfactants, polyoxyalkylene-based surfactants and mixtures thereof.

13. The homogenous color-changing composition of claim 1, wherein the color-changing composition includes more than one organic solvent.

14. A multiple-component material, the material comprising:
    a substrate and a printed layer on the substrate, wherein the printed layer includes a homogenous color-changing composition comprising:
    a matrix-forming component;
    a leuco dye;
    a Lewis Acid; and
    a neutral surfactant
    wherein the Lewis Acid is capable of dissociating from the leuco dye when contacted by an aqueous solution, thereby changing the color of the homogeneous color-changing composition.

15. The multiple-component material of claim 14, wherein the substrate is a non-woven material.

16. The multiple-component material of claim 14, wherein the substrate is a polyolefin film.

17. A disposable absorbent article including the multiple-component material of claim 14 as part of an outer cover.

18. The multiple-component material of claim 14, wherein the printed layer is formed on the substrate in one or more patterns selected from stripes, dots, geometric shapes, irregular shapes, alpha-numeric characters, anthropomorphic images, pictorial representation of animals, pictorial representation of inanimate objects, cartoon characters, logos and trademarks.

19. A disposable absorbent article including a multiple-component material, the material comprising: a substrate and a film layer on the substrate, wherein the film layer includes a color-changing composition comprising:

20% to 95% of a matrix-forming component;
0.1% to 10% of a leuco dye;
1% to 20% of a Lewis Acid; and
2% to 50% of a neutral surfactant wherein the Lewis Acid is capable of dissociating from the leuco dye when contacted by an aqueous solution, thereby causing a color-change of the homogeneous color-changing composition.

* * * * *